(12) United States Patent
Ek et al.

(10) Patent No.: US 7,828,853 B2
(45) Date of Patent: Nov. 9, 2010

(54) ARTICULAR SURFACE IMPLANT AND DELIVERY SYSTEM

(75) Inventors: Steven W. Ek, Bolton, MA (US); Anthony Miniaci, Bentleyville, OH (US)

(73) Assignee: Arthrosurface, Inc., Franklin, MA (US)

( * ) Notice: Subject to any disclaimer, the term of this patent is extended or adjusted under 35 U.S.C. 154(b) by 1203 days.

(21) Appl. No.: 11/359,892

(22) Filed: Feb. 22, 2006

(65) Prior Publication Data

US 2007/0005143 A1      Jan. 4, 2007

Related U.S. Application Data

(60) Provisional application No. 60/654,928, filed on Feb. 22, 2005.

(51) Int. Cl.
     *A61F 2/38*      (2006.01)
(52) U.S. Cl. .................................... 623/20.32
(58) Field of Classification Search .............. 606/80, 606/86 R, 87, 88, 96; 623/13.11–13.14
     See application file for complete search history.

(56) References Cited

U.S. PATENT DOCUMENTS

| | | | |
|---|---|---|---|
| 992,819 A | 5/1911 | Springer | |
| 1,451,610 A | 4/1923 | Gestas | |
| 2,267,925 A | 12/1941 | Johnston | |
| 3,176,395 A | 4/1965 | Warner et al. | |
| 3,840,905 A | 10/1974 | Deane | |
| 4,016,651 A | 4/1977 | Kawahara et al. | |
| 4,034,418 A | 7/1977 | Jackson et al. | |
| 4,044,464 A | 8/1977 | Schiess et al. | |
| 4,158,894 A | 6/1979 | Worrell | |
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |

(Continued)

FOREIGN PATENT DOCUMENTS

AU    2001262308    12/2001

(Continued)

OTHER PUBLICATIONS

International Search Report with Written Opinion dated Nov. 29, 2006 received in corresponding International Patent Application Serial No. PCT/US05/23200 (7 pages).

(Continued)

*Primary Examiner*—Thomas C Barrett
*Assistant Examiner*—Michael J Araj
(74) *Attorney, Agent, or Firm*—Grossman Tucker Perreault & Pfleger PLLC

(57) ABSTRACT

A method is provided for delivering an implant for replacing a portion of an articular surface. The method may include forming a socket in an articulating feature that is capable of moving relative to the articular surface. An implant may be placed in the socket and the articulating feature may be moved relative to the articular surface to generally align the socket with an implant site formed in the articular surface. The implant may be transferred from the socket into the implant site.

20 Claims, 7 Drawing Sheets

U.S. PATENT DOCUMENTS

| | | |
|---|---|---|
| 4,535,768 A | 8/1985 | Hourahane et al. |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,712,545 A | 12/1987 | Honkanen |
| 4,714,478 A | 12/1987 | Fischer |
| 4,719,908 A | 1/1988 | Averill et al. |
| 4,729,761 A | 3/1988 | White |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,927,421 A | 5/1990 | Goble et al. |
| 4,938,778 A | 7/1990 | Ohyabu et al. |
| 4,940,467 A | 7/1990 | Tronzo |
| 4,976,037 A | 12/1990 | Hines |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,053,049 A | 10/1991 | Campbell |
| 5,100,405 A | 3/1992 | McLaren |
| 5,127,920 A | 7/1992 | MacArthur |
| 5,192,291 A | 3/1993 | Pannek, Jr. |
| 5,201,881 A | 4/1993 | Evans |
| 5,211,647 A | 5/1993 | Schmieding |
| 5,224,945 A | 7/1993 | Pannek, Jr. |
| 5,255,838 A | 10/1993 | Gladdish, Jr. et al. |
| 5,263,498 A | 11/1993 | Caspari et al. |
| 5,263,987 A | 11/1993 | Shah |
| 5,282,863 A | 2/1994 | Burton |
| 5,290,313 A | 3/1994 | Heldreth |
| 5,312,411 A | 5/1994 | Steele |
| 5,314,478 A | 5/1994 | Oka et al. |
| 5,314,482 A | 5/1994 | Goodfellow et al. |
| 5,336,224 A | 8/1994 | Selman |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,401 A | 3/1995 | Bahler |
| 5,409,494 A | 4/1995 | Morgan |
| 5,413,608 A | 5/1995 | Keller |
| 5,423,822 A | 6/1995 | Hershberger |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,520,695 A | 5/1996 | Luckman |
| 5,522,900 A | 6/1996 | Hollister |
| 5,534,031 A | 7/1996 | Matsuzaki et al. |
| 5,540,696 A | 7/1996 | Booth, Jr. et al. |
| 5,580,353 A | 12/1996 | Mendes et al. |
| 5,593,450 A | 1/1997 | Scott et al. |
| 5,595,193 A | 1/1997 | Walus et al. |
| 5,601,550 A | 2/1997 | Esser |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,645,598 A | 7/1997 | Brosnahan, III |
| 5,681,311 A | 10/1997 | Foley et al. |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Viatle |
| 5,700,264 A | 12/1997 | Zucherman et al. |
| 5,700,265 A | 12/1997 | Romano |
| 5,702,401 A | 12/1997 | Shaffer |
| 5,702,465 A | 12/1997 | Burkinshaw |
| 5,702,467 A | 12/1997 | Gabriel et al. |
| 5,741,266 A | 4/1998 | Moran et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,810,851 A | 9/1998 | Yoon |
| 5,817,095 A | 10/1998 | Smith |
| 5,824,105 A | 10/1998 | Ries et al. |
| RE36,020 E | 12/1998 | Moore et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,928,239 A | 7/1999 | Mirza |
| 5,928,286 A | 7/1999 | Ashby et al. |
| 5,964,752 A | 10/1999 | Stone |
| 5,964,768 A | 10/1999 | Huebner |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,045,564 A | 4/2000 | Walen |
| 6,052,909 A | 4/2000 | Gardner |
| 6,059,831 A | 5/2000 | Braslow |
| 6,071,310 A | 6/2000 | Picha et al. |
| 6,081,741 A | 6/2000 | Hollis |
| 6,086,593 A | 7/2000 | Bonutti |
| 6,102,948 A | 8/2000 | Brosnahan, III |
| 6,120,542 A | 9/2000 | Camino et al. |
| 6,132,433 A | 10/2000 | Whelan |
| 6,146,385 A | 11/2000 | Torrie et al. |
| 6,149,654 A | 11/2000 | Johnson |
| 6,159,216 A | 12/2000 | Burkinshaw et al. |
| 6,165,223 A | 12/2000 | Metzger et al. |
| 6,168,626 B1 | 1/2001 | Hyon et al. |
| 6,171,340 B1 | 1/2001 | McDowell |
| 6,193,724 B1 | 2/2001 | Chan |
| 6,206,885 B1 | 3/2001 | Ghahremani et al. |
| 6,217,549 B1 | 4/2001 | Selmon et al. |
| 6,217,619 B1 | 4/2001 | Keller |
| 6,235,060 B1 | 5/2001 | Kubein-Meesenburg |
| 6,251,143 B1 | 6/2001 | Schwartz et al. |
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |

| | | | | | | |
|---|---|---|---|---|---|---|
| 6,358,253 | B1 | 3/2002 | Torrie et al. | 2003/0181878 A1 | 9/2003 | Tallarida et al. |
| 6,375,658 | B1 | 4/2002 | Hangody et al. | 2003/0204195 A1 | 10/2003 | Keane et al. |
| 6,383,188 | B2 | 5/2002 | Kuslich | 2003/0216669 A1 | 11/2003 | Lang et al. |
| 6,415,516 | B1 | 7/2002 | Tirado et al. | 2003/0225456 A1 | 12/2003 | Ek |
| 6,443,954 | B1 | 9/2002 | Bramlet et al. | 2003/0225457 A1 | 12/2003 | Justin et al. |
| 6,461,373 | B2 | 10/2002 | Wyman et al. | 2004/0015170 A1 | 1/2004 | Tallarida et al. |
| 6,468,309 | B1 | 10/2002 | Lieberman | 2004/0034359 A1 | 2/2004 | Schmieding et al. |
| 6,478,178 | B2 | 11/2002 | Ralph et al. | 2004/0034437 A1 | 2/2004 | Schmieding |
| 6,478,801 | B1 | 11/2002 | Ralph et al. | 2004/0082906 A1 | 4/2004 | Tallarida et al. |
| 6,482,210 | B1 | 11/2002 | Skiba et al. | 2004/0106928 A1 | 6/2004 | Ek |
| 6,494,914 | B2 | 12/2002 | Brown | 2004/0133276 A1 | 7/2004 | Lang et al. |
| 6,520,964 | B2 | 2/2003 | Tallarida et al. | 2004/0138754 A1 | 7/2004 | Lang et al. |
| 6,527,754 | B1 | 3/2003 | Tallarida et al. | 2004/0138758 A1 | 7/2004 | Evans et al. |
| 6,530,956 | B1 | 3/2003 | Mansmann | 2004/0148030 A1 | 7/2004 | Ek |
| 6,537,274 | B1 | 3/2003 | Katz | 2004/0153087 A1 | 8/2004 | Sanford et al. |
| 6,540,786 | B2 | 4/2003 | Chibrac et al. | 2004/0193281 A1 | 9/2004 | Grimes |
| 6,551,322 | B1 | 4/2003 | Lieberman | 2004/0199166 A1 | 10/2004 | Schmieding et al. |
| 6,575,982 | B1 | 6/2003 | Bonutti | 2004/0230315 A1 | 11/2004 | Ek |
| 6,585,666 | B2 | 7/2003 | Suh et al. | 2004/0260303 A1 | 12/2004 | Carrison |
| 6,591,581 | B2 | 7/2003 | Schmieding | 2005/0015153 A1 | 1/2005 | Goble et al. |
| 6,599,321 | B2 | 7/2003 | Hyde et al. | 2005/0038520 A1 | 2/2005 | Binette et al. |
| 6,607,561 | B2 | 8/2003 | Brannon | 2005/0043808 A1 | 2/2005 | Felt et al. |
| 6,610,067 | B2 | 8/2003 | Tallarida | 2005/0065612 A1 | 3/2005 | Winslow |
| 6,679,917 | B2 | 1/2004 | Ek | 2005/0075642 A1 | 4/2005 | Felt |
| 6,746,451 | B2 | 6/2004 | Middleton et al. | 2005/0143731 A1 | 6/2005 | Justin et al. |
| 6,755,837 | B2 | 6/2004 | Ebner | 2005/0143745 A1 | 6/2005 | Hodorek et al. |
| 6,770,078 | B2 | 8/2004 | Bonutti | 2005/0143831 A1 | 6/2005 | Justin et al. |
| 6,783,550 | B2 | 8/2004 | MacArthur | 2005/0154398 A1 | 7/2005 | Miniaci |
| 6,783,551 | B1 | 8/2004 | Metzger | 2005/0209705 A1 | 9/2005 | Niederauer et al. |
| 6,802,864 | B2 | 10/2004 | Tornier | 2005/0229323 A1 | 10/2005 | Mills et al. |
| 6,814,735 | B1 | 11/2004 | Zirngibl | 2005/0287187 A1 | 12/2005 | Mansmann |
| 6,827,722 | B1 | 12/2004 | Schoenefeld | 2006/0004461 A1 | 1/2006 | Justin et al. |
| 6,860,902 | B2 | 3/2005 | Reiley | 2006/0020343 A1 | 1/2006 | Ek |
| 6,884,246 | B1 | 4/2005 | Sonnabend et al. | 2006/0052878 A1 | 3/2006 | Schmieding |
| 6,923,813 | B2 | 8/2005 | Phillips et al. | 2006/0058744 A1 | 3/2006 | Tallarida et al. |
| 6,926,739 | B1 | 8/2005 | OConnor | 2006/0085006 A1 | 4/2006 | Ek |
| 6,962,577 | B2 | 11/2005 | Tallarida et al. | 2006/0149370 A1 | 7/2006 | Schmieding et al. |
| 6,969,393 | B2 | 11/2005 | Pinczewski et al. | 2006/0190002 A1 | 8/2006 | Tallarida |
| 6,989,016 | B2 | 1/2006 | Tallarida et al. | 2006/0195112 A1 | 8/2006 | Ek |
| 7,029,479 | B2 | 4/2006 | Tallarida | 2006/0229726 A1 | 10/2006 | Ek |
| 7,037,341 | B2 * | 5/2006 | Nowakowski ............ 623/20.14 | 2007/0073394 A1 | 3/2007 | Seedhom et al. |
| 7,063,717 | B2 | 6/2006 | St. Pierre et al. | 2007/0093842 A1 | 4/2007 | Schmieding |
| 7,115,131 | B2 | 10/2006 | Engh et al. | 2007/0093890 A1 | 4/2007 | Eliasen et al. |
| 7,156,880 | B2 | 1/2007 | Evans et al. | 2007/0118136 A1 | 5/2007 | Ek |
| 7,160,305 | B2 | 1/2007 | Schmieding | 2007/0123921 A1 | 5/2007 | Ek |
| 7,163,541 | B2 | 1/2007 | Ek | 2007/0179608 A1 | 8/2007 | Ek |
| 7,166,133 | B2 | 1/2007 | Evans et al. | 2007/0233128 A1 | 10/2007 | Schmieding et al. |
| 7,192,431 | B2 | 3/2007 | Hangody et al. | 2007/0250067 A1 | 10/2007 | Schmieding et al. |
| 7,204,839 | B2 | 4/2007 | Dreyfuss et al. | 2007/0255399 A1 | 11/2007 | Eliasen et al. |
| 7,204,854 | B2 | 4/2007 | Guederian et al. | 2007/0265700 A1 | 11/2007 | Eliasen et al. |
| 7,235,107 | B2 | 6/2007 | Evans et al. | 2007/0288031 A1 | 12/2007 | Dreyfuss et al. |
| 7,238,189 | B2 | 7/2007 | Schmieding et al. | 2007/0299519 A1 | 12/2007 | Schmieding |
| 7,241,316 | B2 | 7/2007 | Evans et al. | 2008/0004659 A1 | 1/2008 | Burkhart et al. |
| 7,264,634 | B2 | 9/2007 | Schmieding | 2008/0015709 A1 | 1/2008 | Evans et al. |
| 7,303,577 | B1 | 12/2007 | Dean | 2008/0027430 A1 | 1/2008 | Montgomery et al. |
| 7,311,702 | B2 | 12/2007 | Tallarida et al. | 2008/0033443 A1 | 2/2008 | Sikora et al. |
| 7,510,558 | B2 | 3/2009 | Tallarida | 2008/0086139 A1 | 4/2008 | Bourke et al. |
| 7,569,059 | B2 | 8/2009 | Cerundolo | 2008/0172125 A1 | 7/2008 | Ek |
| 2001/0012967 | A1 | 8/2001 | Mosseri | 2008/0183290 A1 | 7/2008 | Baird et al. |
| 2001/0039455 | A1 | 11/2001 | Simon et al. | 2008/0188935 A1 | 8/2008 | Saylor et al. |
| 2001/0056266 | A1 | 12/2001 | Tallarida et al. | 2008/0275512 A1 | 11/2008 | Albertorio et al. |
| 2002/0055783 | A1 | 5/2002 | Tallarida et al. | 2008/0306483 A1 | 12/2008 | Iannarone |
| 2002/0106393 | A1 | 8/2002 | Bianchi et al. | 2009/0198288 A1 | 8/2009 | Hoof et al. |
| 2002/0138150 | A1 | 9/2002 | Leclercq | 2009/0234452 A1 | 9/2009 | Steiner et al. |
| 2002/0147498 | A1 | 10/2002 | Tallarida et al. | | | |
| 2003/0028196 | A1 | 2/2003 | Bonutti | | FOREIGN PATENT DOCUMENTS | |
| 2003/0060887 | A1 | 3/2003 | Ek | | | |
| 2003/0065391 | A1 | 4/2003 | Re et al. | AU 2003262428 | 8/2009 | |
| 2003/0105465 | A1 | 6/2003 | Schmieding et al. | DE 2933174 | 4/1980 | |
| 2003/0120276 | A1 | 6/2003 | Tallarida et al. | DE 3516743 | 11/1986 | |
| 2003/0120278 | A1 | 6/2003 | Morgan et al. | DE EP1335684 | * 8/2003 | |
| 2003/0130741 | A1 | 7/2003 | McMinn | EP 0350780 | 7/1989 | |
| 2003/0171756 | A1 | 9/2003 | Fallin et al. | EP 0350780 | 1/1990 | |

| | | |
|---|---|---|
| EP | 0485678 | 5/1992 |
| EP | 0327387 | 9/1992 |
| EP | 0505634 | 9/1992 |
| EP | 0903125 | 3/1999 |
| EP | 0903127 | 3/1999 |
| EP | 0661023 | 8/2001 |
| EP | 1426013 | 9/2004 |
| EP | 1278460 | 4/2009 |
| FR | 2242068 | 3/1975 |
| FR | 2642301 | 3/1990 |
| FR | 2676917 | 12/1992 |
| FR | 2718014 | 10/1995 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 9920192 | 4/1999 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 2004014261 | 2/2004 |
| WO | 2004026170 | 4/2004 |
| WO | 2004075777 | 9/2004 |
| WO | 2005051231 | 6/2005 |
| WO | 2006004885 | 1/2006 |
| WO | 2006091686 | 8/2006 |

OTHER PUBLICATIONS

U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (date unknown).
International Preliminary Report on Patentability dated Mar. 1, 2007 in corresponding International Patent Application No. PCT/US2005/030120 (6 pages).
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Nov. 27, 2006 issued in corresponding PCT patent application No. PCT/US06/00380.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
Office Action issued in corresponding U.S. Appl. No. 10/741,044 dated Oct. 26, 2005.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.

USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, in related EPO application No. 03 026 286.9 (4 pgs).
EPO Office Action dated Mar. 15, 2005, in related EPO application No. 03 026 286.9, (3 pgs).
EPO Search Report in related EPO Application No. 03 02 6286.9 dated Feb. 26, 2004 (5pgs).
EPO Search Report in related EPO Application No. 03 02 6286.9 dated Apr. 27, 2004 (6pgs).
Examination Report dated Feb. 22, 2005 in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
ATOS News, Habermeyer, "The artificial limb "Eclipse"—A new draft without shank in the implantation of artificial shoulder limbs" dated Jan. 13, 2006 (5 pages).
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action in related U.S. Appl. No. 11/169,326 dated Jun. 30, 2008.
U.S. Office Action in related U.S. Appl. No. 11/169,326 dated Jul. 27, 2007.
U.S. Office Action in related U.S. Appl. No. 11/169,326 dated Apr. 17, 2007.
U.S. Office Action in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
Thermann, et al, ATOS Newsletter, Jun. 2005, Aktuelle Themen, (16 pages).
Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.

Chainsaw, Wikipedia, the free encyclopedia, http://en.wikipedia.org/w/index.php?title=Chainsaw&printable=yes, Jun. 26, 2007 (3 pages).

Cannulated Hemi Implants from Vielex, (3 pages).

APTA | Knee,/http://www.apta.org/AM/PrinerTemplate.cfm?Section=Home&TEMPLATE=/CM/HTMLDisplay.dfg&... Jun. 25, 2007 (1page).

Arthrosurface, Restoring the Geometry of Motion, HemiCAP Patello—Femoral Resurfacing System (19 pages).

Anatomical Arthroplastie, Total Evolutive Shoulder System T.E.S.S., Biomet France, Biomet Europe (4 pages).

American Machinist, Full-radius milling cutters, http://www.americanmachinist.com/Classes/Article/ArticleDraw_P. aspx, Jun. 26, 2007 (1 page).

Chuck (engineering),Wikipedia, the free encyclopedia, http://en.wikipedia.org/w/index.php?title=Chuck_% 28engineering%29&printable=yes, Jun. 25, 2007, (4 pages).

Dovetail Rails, http://www.siskiyou.com/MDRSeries.htm, Jun. 25, 2007 (2 pages).

Knee Resurfacing, Permedica, GKS, Global Knee System. Cod. 104570 vers 1.0 del Mar. 15, 2006 (8pages).

Major Biojoint System, La nuova frontiera della biointegrazione naturale, Finceramica Biomedical solutions (4 pages).

Makita Industrial Power Tools, Product Details Print Out, Chain Mortiser, http://www.makita.com/menu.php? pg=product_det_prn&tag=7104L, Jun. 26, 2007 (3pgs).

Milling machine, Wikipedia, the free encyclopedia, http://en.wikipedia.org/w/index.php?title=Milling_machine&printable=yes, Jun. 26, 2007 (4 pages).

Mortise and tenon, Wikipedia, the free encyclopedia, http://en.wikipedia.org/w/index.php?title=Mortise_and_tenon&printable=yes, Jun. 25, 2007 (3 pages).

Oka et al, "Development of artificial articular cartilage", Proc Instn Mech Engrs vol. 214 Part H, 2000 pp. 59-68 (10 pages).

Reversed Arthroplastie, Total Evolutive Shoulder System T.E.S.S., Biomet France, Biomet Europe (4 pages).

M. Siguier, MD et al, "Preliminary Results of Partial Surface Replacement of the Femoral Head in Osteonecrosis", The Jorunal of Arthroplasty, vol. 14, No. 1, 1999, pp. 45-51.

T. Siguier, MD et al, Partial Resurfacing Arthroplasty of the Femoral Head in Avascular Necrosis, Clinical Orthopaedics and Related Research, No. 386, 2001, pp. 85-92.

Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).

The Mini Uni: A New Solution for Arthritic Knew Pain and Disability, AORI, 4 pages, www.aori.org/uniknee.htm Apr. 20, 2004.

The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.

Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).

Russell E. Windsor, MD, In-Depth Topic Reviews, Unicompartmental Knee Replacement, Nov. 7, 2002, 9 pages.

Yaw angle, Wikipedia, the free encyclopedia, http://en.wikipedia.org/w/index.php?title=Yaw_angle&printable=yes, Jun. 25, 2007 (1 page).

Bale, MD, Reto J., et al, "Osteochondral Lesions of the Talus: Computer=assisted Retrograde Drilling Feasibility and Accuracy in Initial Experriences[1]", (Radiology. 2001;218:278-282) @ RSNA, 2001.

Biomet/Copeland, "Aequalis® Resurfacing Head" Tornier, Scientific Vision, Surgical Leadership, SS-401 Jan. 2007.

Kumai, M.D., Tsukasa, et al Arthroscopic Drilling for the Treatment of Osteochondral Lesions of the Talus*, The Journal of Bone & Joint Surgery, American vol. 81:1229-35(1999).

Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug. 2001),:pp. 653-659.

Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

Schneider, T., et al, "Arthroscopy of the ankle joint. A list of indications and realistic expectations", Foot and Ankle Surgery 1996 2:189-193, ® 1996 Arnette Blackwell SA.

Taranow WS, et al, "Retrograde drilling of osteochondral lesions of the medial talar dome", PubMed, www.pubmed.gov, A service of the National Library of Medicing and the Natinal Institutes of Health, Foot Ankle Int.Aug. 1999; 20 (8):474-80.

Ueblacker, M.D., Peter, et al, "Retrograde Cartilage Transplantation of the Proximal and Distal Tibia", Arthroscopy: The Journal of Arthroscipic and Related Surgery, vol. 20, No. 1 (Jan. 2004),: pp. 73-78.

International Search Report with Written Opinion dated Sep. 29, 2006 in corresponding International Patent Application Serial No. PCT/US05/30120 (9 pages).

McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).

Bushnell, et al., "Bony Instability of the Shoulder," Arthroscopy, The Journal of Arthroscopic and related Surgery, vol. 24, No. 9; Sep. 2005 (pp. 1061-1073).

Scalise, et al., "Resurfacing Arthroplasty of the Humerus: Indications, Surgical Technique, and Clinical Results," Techniques in Shoulder and Elbow Surgery 8(3):152-160; 2007.

Davidson, et al., "Focal Anatomic Patellofemoral Inlay Resurfacing: Theoretic Basis, Surgical Technique, and Case Reports," Orthop. Clin. N. Am., 39 (2008) pp. 337-346.

Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).

Uribe, et al., "Partial Humeral Head Resurfacing for Osteonecrosis," Journal of Shoulder and Elbow Surgery, (2009) 6 pages.

Burks, "Implant Arthroplasty of the First Metatarsalphalangeal Joint," Clin. Podiatr. Med. Surg., 23 (2006) pp. 725-731.

Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).

Sullivan, "Hallux Rigidus: MTP Implant Anthroplasty," Foot Ankle Clin. N. Am. 14 2009) pp. 33-42.

Cook et al., "Meta-analysis of First Metatarsophalangeal Joint Implant Arthroplasty," Journal of Foot and Ankle Surgery, vol. 48, Issue 2, pp. 180-190 (2009).

Derner, "Complications and Salvage of Elective Central Metatarsal Osteotomies," Clin. Podiatr. Med. Surg. 26 (2009) 23-35.

Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.

Beecher, et al. "Effects of a contoured articular prosthetic device on tibiofemoral peak contact pressure: a biomechanical study," Knee Surg Sports Traumatol Arthrosc. Jan. 2008; 16(1):56-63.

European Search Report dated Apr. 22, 2009 issued in related European Patent Application No. 09002088.4.

United States Office Action dated May 8, 2009 issued in related U.S. Appl. No. 11/209,170.

United States Office Action dated May 1, 2009 issued in related U.S. Appl. No. 11/461,240.

Australian Office Action dated Jan. 29, 2009 issued in related Australian Patent Application No. 2004216106.

U.S. Office Action dated Aug. 30, 2006 issued in related U.S. Appl. No. 10/618,887.

U.S. Office Action dated Jan. 15, 2008 issued in related U.S. Appl. No. 10/618,887.

U.S. Office Action dated May 18, 2009 issued in related U.S. Appl. No. 11/209,170.
U.S. Office Action dated May 28, 2009 issued in related U.S. Appl. No. 11/359,891.
Notice of Allowance dated Feb. 20, 2009 issued in related U.S. Appl. No. 10/618,887.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.
Notice of Allowance dated Aug. 27, 2009 issued in related U.S. Appl. No. 10/760,965.
Notice of Allowance dated Aug. 25, 2009 issued in related U.S. Appl. No. 11/379,151.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
Supplemental Notice of Allowance dated Nov. 25, 2009 issued in related U.S. Appl. No. 10/373,463.
Office Action dated Dec. 24, 2009 issued in related U.S. Appl. No. 10/994,453.
Notice of Reasons for Rejection dated Nov. 17, 2009 issued in Japanese Patent Application No. 2007-519417.
European Search Report dated Dec. 3, 2009 issued in related European Patent Application No. 06735827.5.
European Office Action dated Jan. 11, 2010 issued in related European Patent Application No. 2005218302.
U.S. Office Action dated Jan. 25, 2010 issued in related U.S. Appl. No. 11/326,133.

* cited by examiner

ARTICULAR SURFACE IMPLANT AND DELIVERY SYSTEM

CROSS-REFERENCE TO RELATED APPLICATIONS

This application claims the benefit of U.S. provisional patent application Ser. No. 60/654,928, filed on Feb. 22, 2005, and is related to U.S. patent application Ser. No. 10/994,453, filed Nov. 22, 2004, the entire disclosures of which are incorporated herein by reference.

FIELD

The present disclosure is directed at implants for replacing a portion of an articular surface of a joint and systems and method for delivering implants to an implant site.

BACKGROUND

Articular cartilage, found at the ends of articulating bone in the body, is typically composed of hyaline cartilage, which has many unique properties that allow it to function effectively as a smooth and lubricious load bearing surface. Hyaline cartilage problems, particularly in knee, hip joints, and should joints, are generally caused by disease such as occurs with rheumatoid arthritis or wear and tear (osteoarthritis), or secondary to an injury, either acute (sudden), or recurrent and chronic (ongoing). Such cartilage disease or deterioration can compromise the articular surface causing pain and eventually, loss of joint movement. As a result, various methods have been developed to treat and repair damaged or destroyed articular cartilage.

For smaller defects, traditional options for this type of problem include leaving the lesions or injury alone and living with it, or performing a procedure called abrasion arthroplasty or abrasion chondralplasty. The principle behind this procedure is to attempt to stimulate natural healing. The bone surface is drilled using a high speed rotary burr or shaving device and the surgeon removes about 1 mm of bone from the surface of the lesion. This creates an exposed subchondral bone bed that will bleed and will initiate a fibrocartilage healing response. One problem with this procedure is that the exposed bone is not as smooth as it originally was following the drilling and burring which tends to leave a series of ridges and valleys, affecting the durability of the fibrocartilage response. Further, although this procedure can provide good short term results, (1-3 years), fibrocartilage is seldom able to support long-term weight bearing and is prone to wear, soften and deteriorate.

Another procedure, called Microfracture incorporates some of the principles of drilling, abrasion and chondralplasty. During the procedure, the calcified cartilage layer of the chondral defect is removed. Several pathways or "microfractures" are created to the subchondral bleeding bone bed by impacting a metal pick or surgical awl at a minimum number of locations within the lesion. By establishing bleeding in the lesion and by creating a pathway to the subchondral bone, a fibrocartilage healing response is initiated, forming a replacement surface. Results for this technique may be expected to be similar to abrasion chondralplasty. Another means used to treat damaged articular cartilage is a cartilage transplant. Essentially, this procedure involves moving cartilage from an outside source or other knee or from within the same knee into the defect. Typically, this is done by transferring a peg of cartilage with underlying bone and fixing it in place with a screw or pin or by a press fit. Although useful for smaller defects, large defects present a problem, as this procedure requires donor pegs proportionate to the recipient bed. Large diameter lesions may exceed the capacity to borrow from within the same knee joint and rule out borrowing from another source.

Larger defects, however, generally require a more aggressive intervention. Typically treatment requires replacing a portion or all of the articular surface with an implant or prosthetic having an outer layer that that is polished or composed of a material that provides a lubricious load bearing surface in approximation of an undamaged cartilage surface. Replacement of a portion, or all, of the articular surface requires first cutting, boring, or reaming the damaged area to remove the damaged cartilage. A recess to receive an implant or prosthetic is formed at the damaged site. The implant or prosthetic is then secured to the bone in an appropriate position in the recess.

The treatment and/or replacement procedure often requires direct access to the damaged surface of the cartilage. While the most commonly damaged portions of some joints may easily be accessed for repair using a minimally invasive procedure some joints are not nearly as accessible. For example, the superior or medial femoral head, the medial humeral head, the glenoid, etc. do not permit direct access sufficient to carry out replacement of the articular surface in a minimally invasive manner. In fact, repair of such obstructed joints often requires an invasive procedure and necessitates complete dislocation of the joint. Procedures of such an invasive nature may be painful and require an extended recovery period.

completely dislocating the joint.

BRIEF DESCRIPTION OF THE DRAWINGS

Features and advantages of the disclosed subject matter will be apparent from the following descriptions of embodiments consistent therewith, which description should be considered in conjunction with the accompanying drawings, wherein.

DETAILED DESCRIPTION

Figure 1:
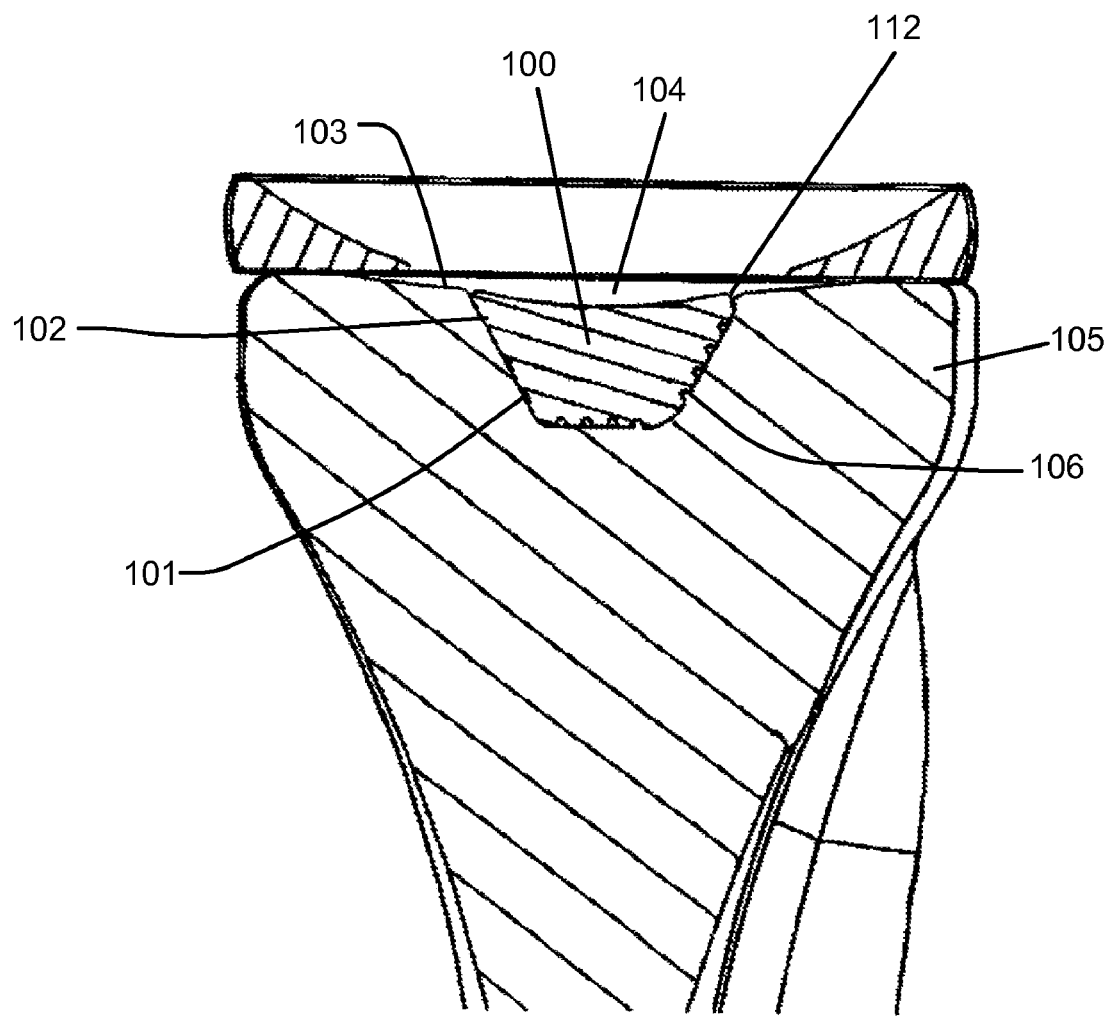
FIG. 1 is a cross-sectional view of an embodiment of an implant consistent with the present disclosure positioned to replace a portion of an articular surface.
Figure 2:
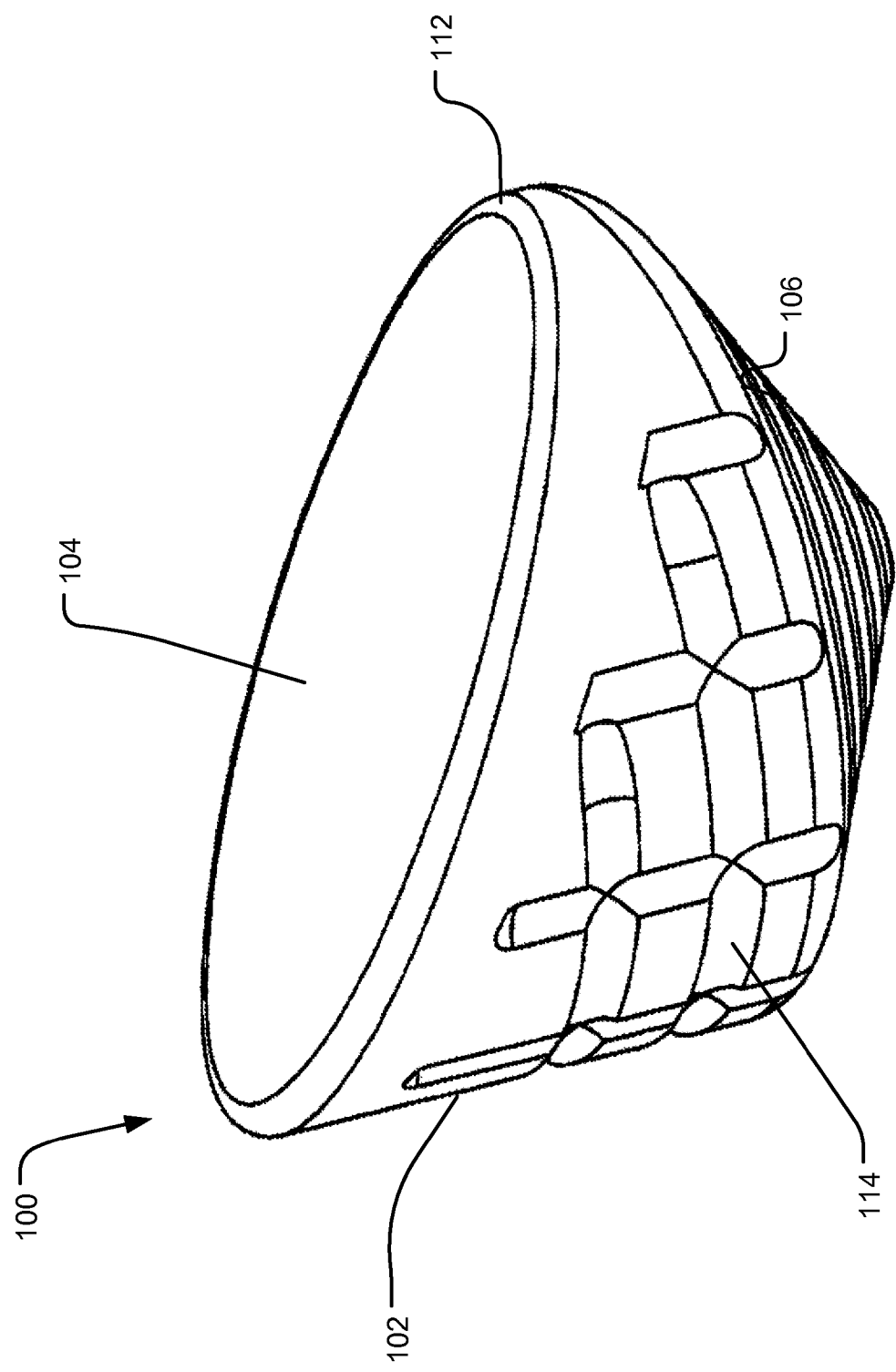
FIG. 2 is a top perspective view of an embodiment of an implant consistent with the present disclosure.

FIGS. 1 through 4 illustrate an embodiment of an implant 100 consistent with the present disclosure from various views. In FIG. 1 the implant 100 is shown installed in an implant site 101 and replacing at least a portion of an articular surface 103, e.g. of a bone 105. In the illustrated embodiment of FIG. 1 the bone 105 is generally show as being a tibia. The implant 100 is depicted replacing at least a portion of the articular surface of the tibia corresponding to a portion of the knee joint. While an implant herein may suitably be employed to replace a portion of an articular surface of a knee joint, the present disclosure should not be interpreted as being limited to replacing a portion of a tibial articular surface in a knee joint. An implant herein may suitably be employed to replace at least a portion of other articular surfaces without limitation.

As shown, the implant 100 may generally include an implant body 102. The implant body 102 may include a load bearing surface 104 at one end of the implant body 102. The load bearing surface 104 may be a surface configured to interact with a cooperating articulating feature. The proximal end 106 of the implant body 102, opposite the load bearing surface 104, may be provided having a generally tapered and/or conical profile. In further embodiments, the proximal end 106 may have a generally truncated conical profile.

Figure 3:
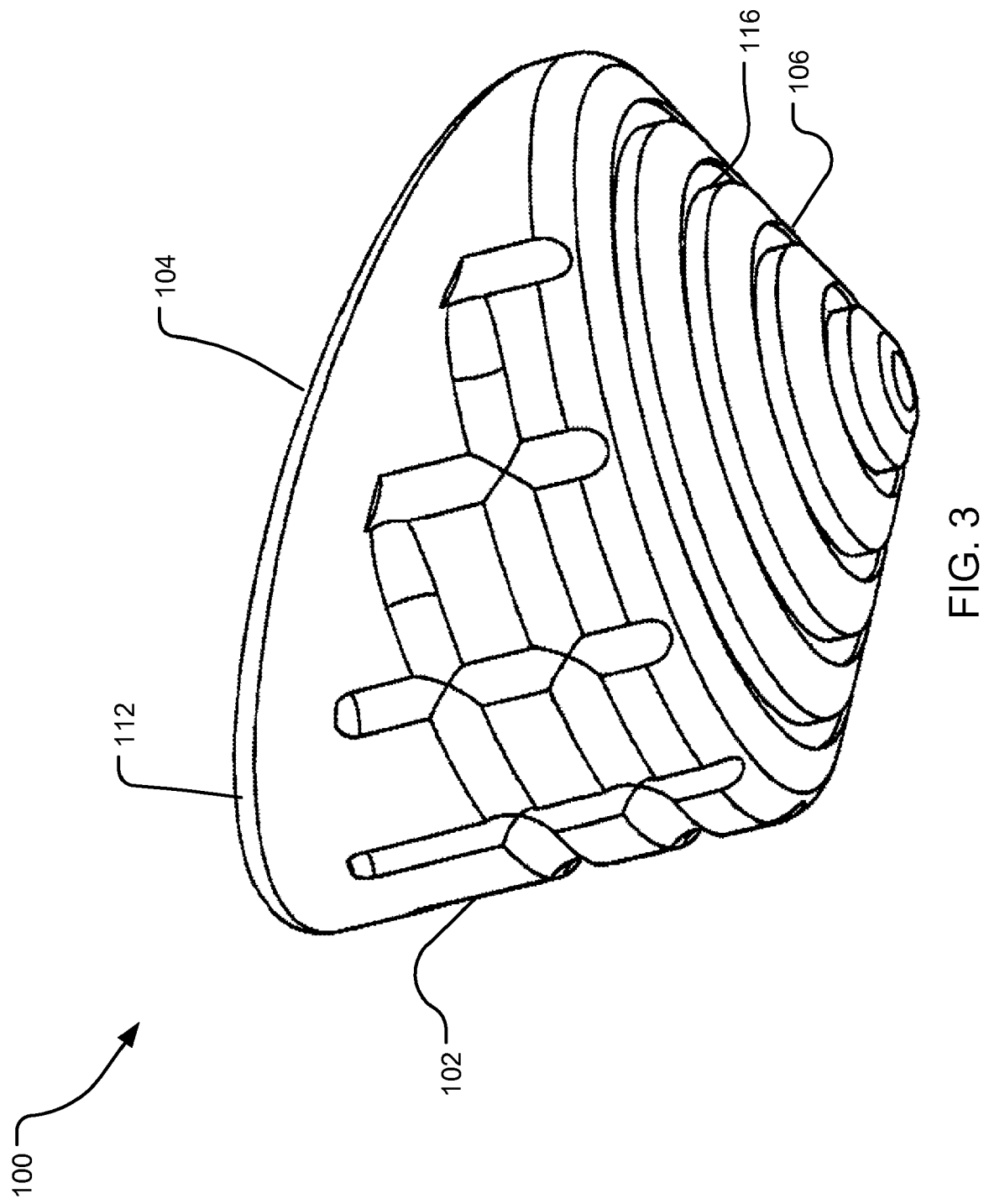
FIG. 3 is a bottom perspective of an embodiment of an implant consistent with the present disclosure.

As best shown in FIG. 3, the implant body 102 may have a generally cylindrical shape. Accordingly, the implant 100 may have a generally circular cross-sectional shape and may be axially symmetrical. In other embodiments, the implant may have an oval or other cross-sectional shape. Consistent with the illustrated embodiment, the load bearing face 104 of the implant 100 may be oriented at an angle relative to the axis of the cylindrical implant body 102. As best observed in FIGS. 2 and 4, the angular orientation of the load bearing surface 104 relative to the axis of the implant body 102 may provide the load bearing surface 104 having a generally elliptical and/or oval shape.

The angular relationship of the load bearing surface 104 relative to the axis of the implant body 102 may be varied according to specific applications. According to one aspect, the angle of the load bearing surface 104 relative to the axis of the implant body 102 may be related to the configuration and/or angle of the implant site 101 to the portion of the articular surface 103 to be replaced. Accordingly, depending upon the relationship between the portion of the articular surface 103 to be replaced and the implant site 101, the angular relationship between the load bearing surface 104 and the axis of the implant body 102 may vary between a very shallow angle, e.g., less than 45 degrees, up to a perpendicular orientation. In the specific illustrated embodiment, the load bearing surface 104 may be at an angle of about 60 degrees relative to the implant body 102. As the angle of the load bearing surface 104 relative to the implant body 102 is application specific, an implant 100 consistent with the present disclosure should not be considered to be limited by any particular angular relationship.

From a general perspective, the load bearing surface 104 may have a contour and/or geometry that may be capable of cooperating with an interacting articulating surface and/or feature. In one embodiment, the interacting articulating surface and/or feature may include an interacting articular surface of a joint. For example, in an embodiment in which the implant may be employed to replace at least a portion of an articular surface of a tibia, the load bearing surface of the implant may have a contour and/or geometry that may be capable of cooperating with an interacting articular surface of a femur. According to a further embodiment, such as may occur in a uni-compartmental and/or total knee replacement, the implant may be employed to replace at least a portion of the articular surface of a tibia. The load bearing surface of the implant may have a geometry capable of cooperating with an interacting implant replacing at least a portion of an articular surface of a femur. Consistent with the present disclosure, the implant may suitable be employed to replace at least a portion of various articular surfaces in addition to a portion of an articular surface of a tibia. For example, an implant herein may suitably be employed to replace a portion of an articular surface of a knee joint, a hip joint, a shoulder joint, etc. Accordingly, the foregoing example should not be construed as limiting on the application of an implant consistent with the present disclosure.

Consistent with the foregoing, an implant may include a load bearing surface having a contour and/or geometry that may be capable of cooperating with an interacting articulating surface. As such, the load bearing surface may have a contour and/or geometry that may generally approximate and/or be based on a contour and/or geometry of the portion of the articular surface being replaced by the implant. In an embodiment, the portion of the articular surface being replaced may be mapped using various know techniques to quantitatively and/or qualitatively represent the contour and/or geometry of the portion of the articular surface that may be replaced by the implant. An implant may be constructed and/or selected from a set of implants having various contours and/or geometries. Consistent with such an embodiment, the load bearing surface of the implant may be based on the contour and/or geometry of the portion of the articular surface to be replaced by the implant. In an alternative embodiment, an implant may be fabricated or selected from a set of standard size and/or shape implants to provide a general approximation of the articular surface being replaced. Selection or fabrication of an implant may rely on various degrees of quantitative reference to the articular surface being replaced, including no quantitative reference to the articular surface.

Different articular surfaces and/or different regions of an articular surface may be susceptible to replacement by implants having a load bearing surface various contours and/or geometries. In some applications a convex load bearing surface may be suitable. In other applications a planar, concave, and/or compound curved load bearing surface may provide a suitable implant load bearing surface geometry.

Figure 4:
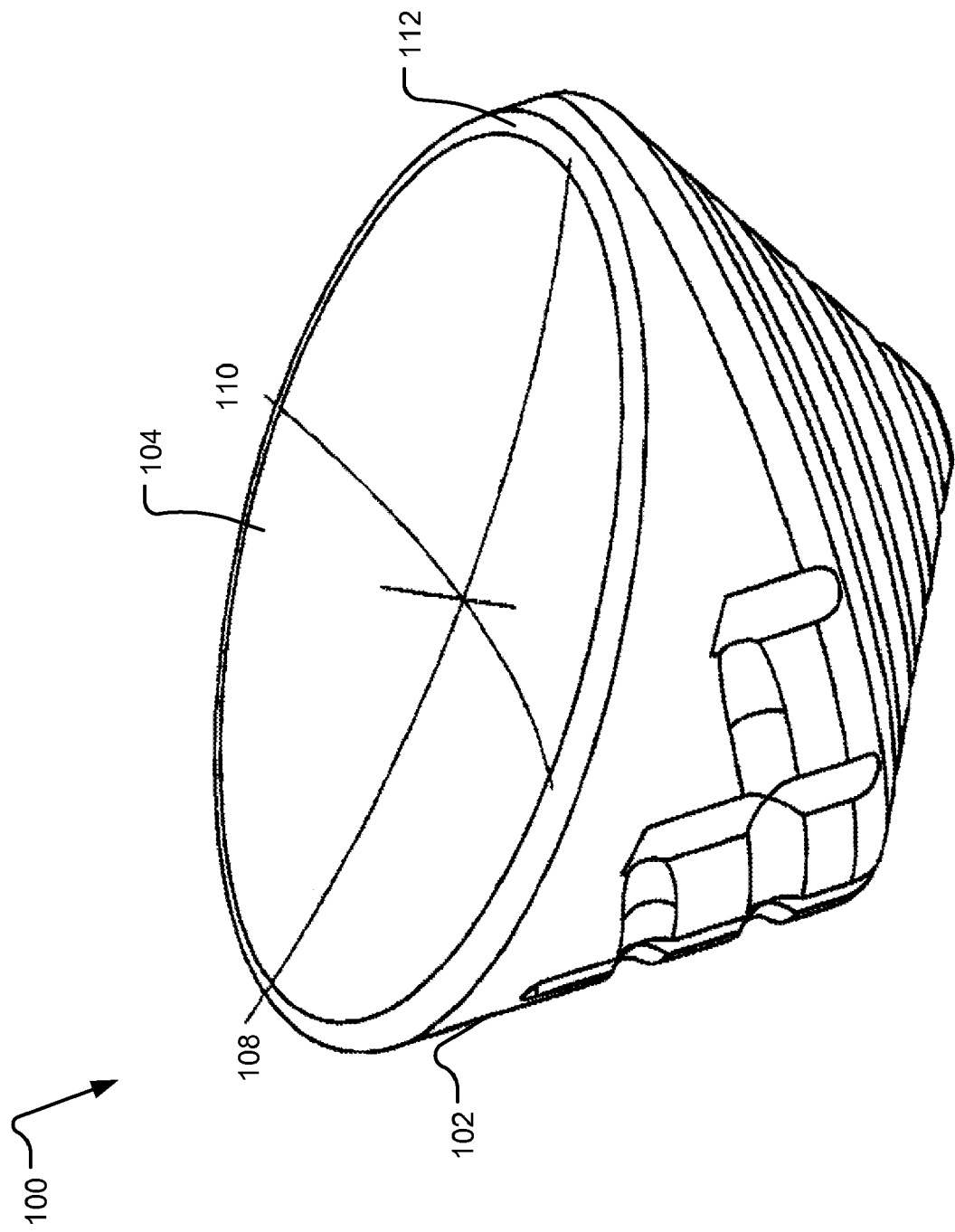
FIG. 4 is a top perspective view of an embodiment of an implant consistent with the present disclosure representationally depicting surface geometry defining contours.

Referring to FIG. 4, the geometry of the load bearing surface 104 of the implant 100 may generally be defined by a first curve 108 and a second curve 110. Consistent with the illustrated embodiment, the first and second curves 108, 110 generally defining the contour and/or geometry of the load bearing surface 104 may have a generally perpendicular orientation to one another. Various other angular relationships between the first and second 108, 110 curves may also suitably be employed. In one embodiment the load bearing surface 104 may have a contour and/or geometry resulting from a faired transition between the first curve 108 and the second curve 110. That is, the contour and/or geometry of the load bearing surface 104 may be provided by a smooth transition between the first curve 108 and the second curve 110 at each quadrant between the first curve 108 and the second curve 110.

According to another embodiment, the load bearing surface 104 may have a contour and/or geometry corresponding to the second curve 110 lofted along the first curve 108. In one such embodiment, the contour and/or geometry of the load bearing surface 104 may be achieved by sweeping the second curve 110 along the first curve 108 while maintaining the second curve 110 normal to the first curve 108. In such an embodiment, the first curve 108 may be provided in a first plane, e.g. a plane defined by the X and Z axis. The second curve 110 may be provided in a perpendicular plane. The angular pitch of the perpendicular plane relative to the first plane may vary along the first curve 108 to maintain the second curve 110 normal to the first curve 108 along the sweep of the first curve 108. According to another embodiment, the second curve 110 may be swept along the first curve 108 with the first curve 108 and the second curve 110 in orthogonal planes. For example, the first curve 108 may be provided in a first plane, e.g., a plane defined by the Y and Z axis and the second curve may be provided in an orthogonal plane, e.g., a plane defined by the X and Z axis.

In one aspect, the first and second curves 108, 110 may generally correspond to measurements of the curvature and/or geometry of the portion of the articular surface 103 to be replaced by the implant 100. In such an embodiment, perpendicular measurements of the contour and/or geometry of the portion of the articular surface 103 to be replaced may be taken. Measurement of the contour and/or geometry of the portion of the articular surface 103 to be replaced by the implant 100 may be achieved using direct contour mapping of the articular surface 103 and/or using various imaging techniques, such as radiological imaging techniques.

The implant 100 may include a relieved edge 112 around the perimeter of the load bearing surface 104. The relieved edge 112 may include a rounded over, e.g., radiused, edge, a chamfer edge, etc. According to one aspect, when the implant 100 is installed in an articular surface 103 and replacing at least a portion of the articular surface 103, the relieved edge 112 around the load bearing surface 104 may reduce the presence of a hard edge at a transition between the implant 100 and surrounding articular surface 103. A reduction and/or elimination of a hard edge at the transition between the load bearing surface 104 of the implant 100 and the surrounding articular surface 103 may reduce and/or eliminate scraping of an interacting articular surface during articulation of the joint. Additionally, the relieved edge 112 may accommodate manufacturing and/or installation tolerances. The relieved edge 112 may permit smooth operation of the joint in a situation in which the implant 100 sits slightly proud above and/or slightly recessed below the surrounding articular surface 103.

As shown, the implant 100 may include a plurality of grooves 114 on the exterior surface of the implant body 102. The grooves 114 may facilitate anchoring the implant 100 in position in an implant site 101 created in the articular surface 103 and the underlying bone 105. Consistent with an embodiment herein, the implant 100 may be secured, at least in part, in the implant site 101 using bone cement. When the implant 100 is installed into the implant site 101 using bone content, the bone cement may be squeezed, forced, and/or caused to flow to at least partially fill at least a portion of one of the grooves 114. The bone cement at least partially filling at least a portion of one of the grooves 114 may provide a mechanical lock between the bone cement and the grooves 114 in the implant body 102. The mechanical lock between the bone cement and the implant 100 may assist in securing the implant 100 in position in the implant site 101. Additionally, the mechanical lock between the bone cement and the grooves 114 may assist in retaining the implant 100 in the implant site 101 in the event of a partial and/or total adhesive failure between the bone cement and the implant.

Similar to the grooves 114 in the implant body 102, the proximal end 106 of the implant 100 may also include one or more grooves 116. The grooves 116 in the proximal end of the implant 100 may provide a mechanical lock between bone cement and the implant 100. In one embodiment, the grooves 114 in the implant body 102 and/or the grooves 116 in the proximal end 106 of the implant 100 may include an undercut region. The undercut region may increase the mechanical lock achieved between the bone cement and the implant 100.

An implant 100 herein may be formed from various different biologically compatible materials. The material of the implant may be selected to provide various properties, combinations of properties, and/or compromises between desired properties. For example, the implant may be formed from a metallic material, such as stainless steel, titanium, and/or various other biologically compatible metals and alloys. Metallic materials may provide strength and wear resistance. The load bearing surface of the implant may be polished to provide a relatively low friction surface for cooperating with an interacting articulating feature. Polymeric and/or polymeric based materials, such as ultra-high molecular weight polyethylene, polyethylene, polyvinyl alcohol hydrogel, etc., may also be employed for producing an implant herein. Such polymeric and/or polymer based materials may provide lubricious and/or low friction surfaces, as may be suitable for cooperating with interacting articular features. Additionally, polymeric and/or polymeric based materials may provide some degree of impact cushioning and/or impact absorption. In still further embodiments, the implant may be provided as an assembly including more than one material. For example, the implant may include a body portion formed from a metallic material having a load bearing surface formed from a polymeric and/or polymeric based material. Various other materials may also suitably be employed for producing an implant herein.

An implant consistent with the present disclosure may be produce using a variety of manufacturing techniques. According to one embodiment, the implant may be produced from cylindrical rod stock. The rod stock may be cut at an angle relative to axis of the rod stock, thereby providing a load bearing surface. The rod stock may further be tapered, e.g., by turning on a lathe, to provide a conical proximal end. Features, such as the grooves in the implant body and the proximal end, as well as the relieved edge of the load bearing surface, may subsequently be machined into the implant. In alternative embodiments, the implant may be produced by machining from a blank and/or billet of material. Furthermore, the implant may be produced using various molding processes, such as metal, ceramic and/or polymer casting. Other molding techniques may include metal injection molding, polymer injection molding, etc. Various other manufacturing processes and techniques may also be employed.

Figure 5:
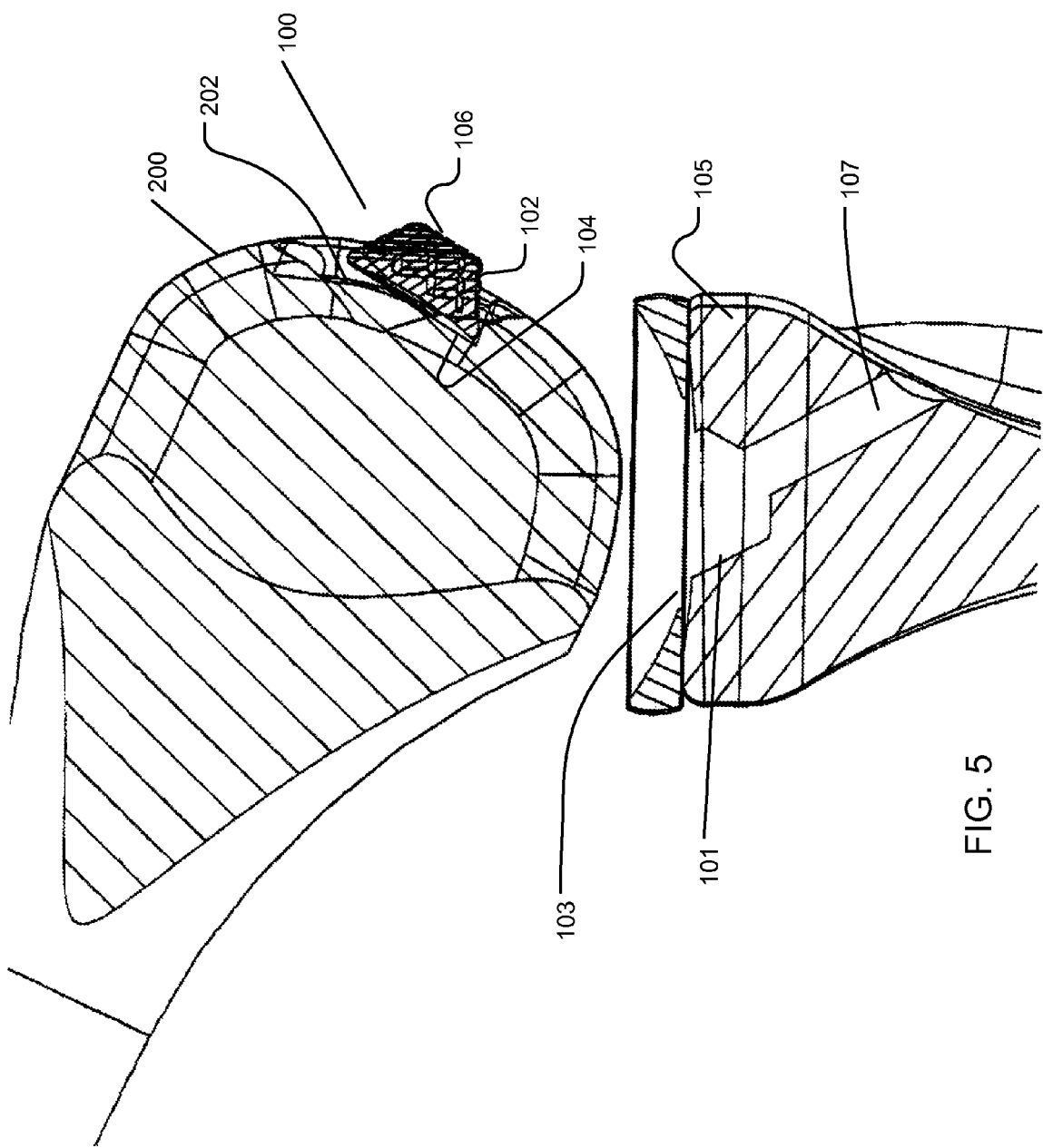
FIG. 5 shows an embodiment of an implant loaded in a socket of a cooperating articulating feature consistent with a system of delivering an implant according to the present disclosure.
Figure 6:
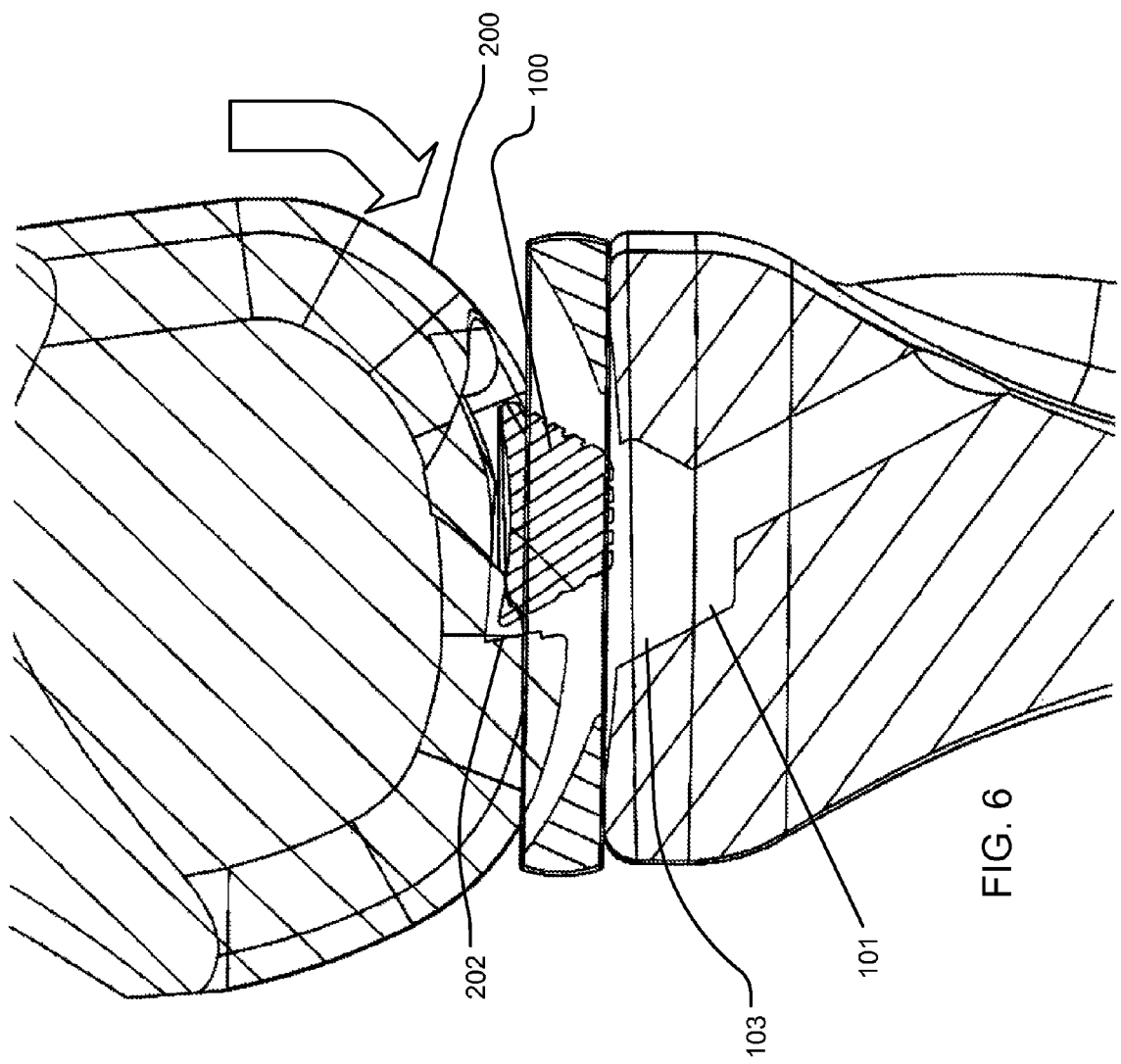
FIG. 6 shows the cooperating articulating feature positioned to align an implant with an implant site in the articular surface consistent with a system of delivering an implant according to the present disclosure.
Figure 7:
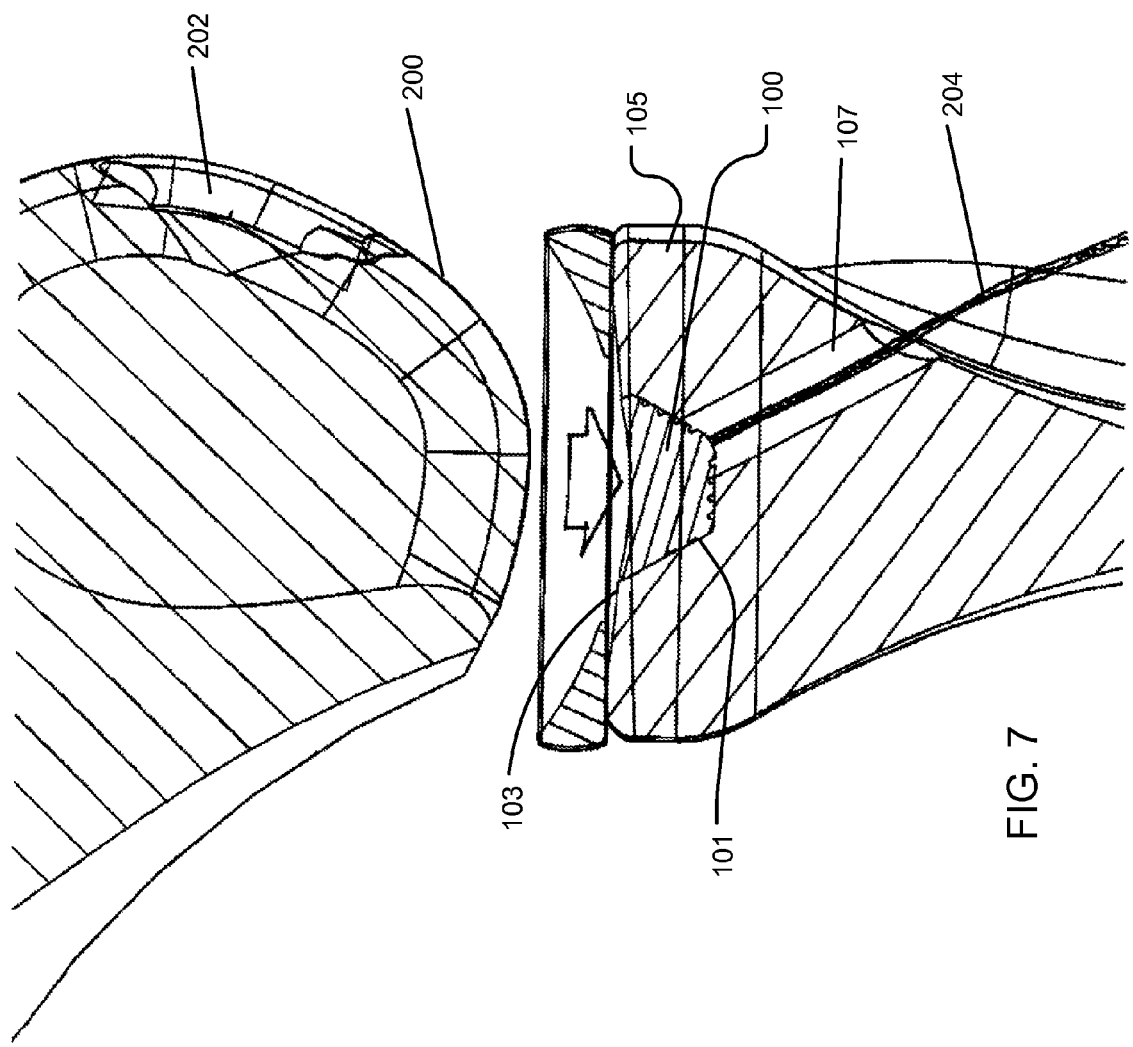
FIG. 7 depicts the installation of an implant according to the present disclosure into an implant site in an articular surface consistent with a system of delivering an implant according to the present disclosure.

Turning next to FIGS. 5 through 7, and embodiment of a system for delivering an implant 100 to an implant site 101 is shown. As depicted, the implant site 101 may be formed in an articular surface 101 and the underlying bone 105. In one embodiment, the implant site 101 may be formed using a retrograde procedure, in which an access tunnel 107 may be created extending through at least a portion of the bone 105. An expanding cutter may be inserted into the access tunnel and a portion of the articular surface 101 and underlying bone 105 may be excised using the expanding cutter. Examples of suitable methods for creating an implant site are disclosed, for example, in U.S. provisional patent application Ser. Nos. 60/683,549, filed on Jun. 28, 2004, and 60/641,552, filed on Jan. 5, 2005. Various other retrograde and/or direct access methods may also suitably be employed for creating an implant site.

Consistent with the illustrated delivery system, the implant 100 may be delivered to the implant site 101 using a cooperating articulating feature 200 as a carrier. In the illustrated embodiment, the implant site 101 may be formed in the articular surface 103 and underlying bone 105 of a tibia. In such and embodiment, the cooperating articulating feature 200 may be an articular surface of a femur. A socket 202, sized to at least partially receive the implant 100, may be formed in the cooperating articulating feature 200. The socket 202 may be formed by drilling, cutting, and/or using other suitable excision techniques.

The cooperating articulating feature 200 may be positioned relative to the articular surface 103 so as to expose the socket 202 in the cooperating articulating feature. In the illustrated embodiment, in which the implant 100 is to be installed in an implant site 101 in a tibia, the knee may be positioned at approximately 80-90 degrees of flexion, thereby exposing the socket formed in the articular surface of the femur. Various other angular relationships may also and/or alternatively suitably be employed. With the socket 202 in the cooperating articulating feature 200 exposed, the implant 100 may be placed in the socket 202. As shown in FIG. 5, the implant 100 may generally be placed in the socket 202 with the load bearing surface 104 facing inward and the implant body 102 and proximal end 106 facing outwardly relative to the socket 202.

Turning to FIG. 6, the cooperating articulating features 200 may be moved relative to the articular surface 103 to generally align the socket 202 in the cooperating articulating feature 200 with the implant site 101 in the articular surface 103. In this manner, the socket 202 in the cooperating articulating feature 200 may generally serve as a carrier for conveying the implant 100 to the implant site 101. In the illustrated embodiment, the knee may be moved to approximately 0-10 degrees of extension. In such an orientation the socket in the femur may be generally aligned with the implant site in the articular surface of the tibia. Depending upon the location of the socket in the femur and the location of the implant site in tibia, the angular orientation, e.g., the angle of extension of a knee, necessary to generally align the socket and the implant site may vary. As such, the angular orientation should not be understood to be limiting on the system herein.

With the socket 202 in the cooperating articulating feature 200 generally aligned with the implant site 101 in the articular surface, the implant 100 may be transferred from the socket 202 to the implant site 103, as shown in FIG. 7. Consistent with the illustrated embodiment, the implant 100 may be transferred to the implant site 101 via a tether 204. As shown, the tether 204 may be coupled to the implant 100 and may extend from the implant site 101 to the exterior of the bone 105 through the access tunnel 107. The tether 204 may be withdrawn through the access tunnel 107, thereby drawing the implant 100 into the implant site 101. According to another embodiment; the implant 100 may be pushed from the socket 202 and seated in the implant site 101 using an implement introduced in between the articular surface 103 and the cooperating articulating feature 200.

As mentioned previously, the implant 100 may be secured in the implant site, at least in part, using bone cement. The bone cement may be applied to the implant 100 and/or to the implant site 101 prior to transferring the implant 100 from the socket 202 to the implant site 101. Alternatively, bone cement may be introduced between the implant 100 and the implant site prior to fully seating the implant 100. The bone cement may be introduced in between the implant 100 and the implant site 101 through the access tunnel 107, and/or from the exterior of the implant site 101 adjacent to the articular surface. Various additional and/or alternative fixturing and/or securement techniques may be employed for securing the implant 100 in position in the implant site 101.

In summary, according to one aspect, the present disclosure may provide a method for delivering an articular surface implant. The method may include forming an implant site in an articular surface, in which the implant site is capable of receiving an implant for replacing at least a portion of the articular surface. The method may also include forming a socket in an articulating feature capable of moving relative to the articular surface, and disposing the implant at least partially in the socket. The method may also include generally aligning the socket and the implant site, and transferring the implant from the socket at least partially into the implant site.

According to another aspect, the present disclosure may provide a method of replacing a portion an articular surface of a tibia. The method may include excising an implant site in the articular surface of the tibia, and excising a socket in an articular surface of a femur adjacent to the tibia. The method may also include disposing an implant capable of replacing at least a portion of the articular surface of the tibia in the socket. The method may further include articulating the femur relative to the tibia to generally align the socket and the implant site, and transferring the implant from the socket at least partially into the implant site.

The illustrated system is directed at delivering an implant for replacing at least a portion of an articular surface of a tibia. In the particular illustrated embodiment, the implant may be accommodated in a socket formed in a femoral articular surface and the femur may be articulated relative to the tibia to generally bring the socket in the formal articular surface into alignment with the implant site in the tibial articular surface. With the socket in the femoral articular surface generally aligned with the implant site in the tibial articular surface, the implant may be transferred from the socket in the femoral articular surface to the implant site in the tibial articular surface. However, from a broader perspective, a system consistent with the present disclosure may generally include disposing an implant in a socket, cutout, or natural recess in a cooperating articulating feature and moving the feature to align the implant in the socket with an implant site in an articular surface and transferring the implant from the socket to the implant site. Accordingly, the system herein is susceptible to broader application than the delivery of an implant to an implant site in an articular surface. For example, the system herein may be used to deliver an implant to an articular surface of a hip joint, shoulder joint, elbow, etc. The scope of the present disclosure should not, therefore, be limited to the specific embodiments disclosed therein.

What is claimed is:

1. A method for delivering an articular surface implant within a joint comprising a first and a second bone having at least a first and a second articular surface, respectively, said method comprising:

forming an implant site in said first articular surface, said implant site configured to receive said articular surface implant for replacing at least a portion of said first articular surface;

forming a socket in an articulating feature associated with said second articular surface of said second bone;

disposing said articular surface implant at least partially in said socket, moving said second bone from a first position, wherein said socket is exposed relative to said first articular surface of said first bone and is configured to receive said articular surface implant, to a second position, wherein said socket is generally aligned with implant site; and pulling said articular surface implant from said socket at least partially into said implant site via a tether extending through an access tunnel extending through said first bone in a direction away from said first articular surface.

2. A method according to claim 1, wherein moving said second bone relative to said first bone comprises articulating said joint.

3. A method according to claim 1, wherein forming said socket in said articulating feature comprises excising at least a portion of said second bone.

4. A method according to claim 1, further comprising securing said articular surface implant in said implant site.

5. The method of claim 1, further comprises forming a tunnel extending from said first articular surface through said first bone to a position disposed beneath said first articular surface.

6. The method of claim 5, wherein forming said implant site in said first articular surface comprises retrograde drilling said first articular surface.

7. The method of claim 5, wherein transferring said implant from said socket at least partially into said implant site further comprises urging said implant into said implant site with a tether extending through said tunnel.

8. The method of claim 1, wherein disposing said articular surface implant at least partially in said socket further comprises disposing said implant within said socket with a load bearing surface facing generally into said socket, said load bearing surface of said implant being configured to replace said at least a portion of said first articular surface.

9. A method of replacing a portion an articular surface of a tibia within a knee joint, said method comprising:
    excising an implant site in said articular surface of said tibia, said excising comprising creating an access tunnel through bone behind, and extending toward, said articular surface of said tibia, and excising at least a portion of said articular surface adjacent to said tunnel;
    excising a socket in an articular surface of a femur adjacent to said tibia;
    disposing at least a portion of an implant within said socket;
    articulating said femur relative to said tibia from a first position, wherein said socket is exposed relative to said articular surface of said tibia and is configured to receive said implant, to a second position, wherein said socket is generally aligned with said implant site; and
    transferring said implant from said socket at least partially into said implant site.

10. A method according to claim 9, wherein transferring said implant comprises pulling said implant into said implant site via said tunnel.

11. A method according to claim 9, wherein disposing said implant in said socket comprises articulating said femur relative to said tibia to exposed said socket.

12. A method according to claim 9, further comprising securing said implant in said implant site.

13. A method for delivering an articular surface implant within a joint comprising a first and a second bone having at least a first and a second articular surface, respectively, said method comprising:
    forming an implant site in said first articular surface, said implant site configured to receive said articular surface implant for replacing at least a portion of said first articular surface;
    forming a socket in an articulating feature associated with said second articular surface of said second bone;
    disposing said articular surface implant at least partially in said socket,
    moving said second bone from a first position, wherein said socket is exposed relative to said first articular surface of said first bone and is configured to receive said articular surface implant, to a second position, wherein said socket is generally aligned with implant site;
    forming a tunnel extending from said first articular surface through said first bone to a position disposed beneath said first articular surface; and
    transferring said articular surface implant from said socket at least partially into said implant site.

14. A method according to claim 13, wherein moving said second bone relative to said first bone comprises articulating said joint.

15. A method according to claim 13, wherein forming said socket in said articulating feature comprises excising at least a portion of said second bone.

16. A method according to claim 13, wherein transferring said articular surface implant from said socket to said implant site comprises pulling said articular surface implant at least partially into said implant site via a tether extending through an access tunnel extending through said first bone in a direction away from said first articular surface.

17. A method according to claim 13, further comprising securing said articular surface implant in said implant site.

18. The method of claim 13, wherein forming said implant site in said first articular surface comprises retrograde drilling said first articular surface.

19. The method of claim 13, wherein disposing said articular surface implant at least partially in said socket further comprises disposing said implant within said socket with a load bearing surface facing generally into said socket, said load bearing surface of said implant being configured to replace said at least a portion of said first articular surface.

20. The method of claim 13, wherein transferring said implant from said socket at least partially into said implant site further comprises urging said implant into said implant site with a tether extending through said tunnel.

* * * * *